(12) United States Patent
Gourley

(10) Patent No.: US 10,259,712 B2
(45) Date of Patent: Apr. 16, 2019

(54) METHOD OF STABILIZING COMPOUNDS IN WATER, WATER COMPOSITIONS THEREBY, AND ARTICLES CONTAINING SAID WATER COMPOSITIONS

(71) Applicant: Robinson B. Gourley, Sarasota, FL (US)

(72) Inventor: Robinson B. Gourley, Sarasota, FL (US)

( * ) Notice: Subject to any disclaimer, the term of this patent is extended or adjusted under 35 U.S.C. 154(b) by 0 days.

(21) Appl. No.: 15/628,712

(22) Filed: Jun. 21, 2017

(65) Prior Publication Data

US 2017/0297914 A1   Oct. 19, 2017

Related U.S. Application Data

(63) Continuation-in-part of application No. 15/161,853, filed on May 23, 2016, now abandoned.

(60) Provisional application No. 62/173,525, filed on Jun. 10, 2015.

(51) Int. Cl.
| | | |
|---|---|---|
| *A61K 33/40* | (2006.01) | |
| *A61L 15/18* | (2006.01) | |
| *A61L 15/46* | (2006.01) | |
| *C01B 11/02* | (2006.01) | |
| *C01B 15/037* | (2006.01) | |

(52) U.S. Cl.
CPC ............ *C01B 15/037* (2013.01); *A61K 33/40* (2013.01); *A61L 15/18* (2013.01); *A61L 15/46* (2013.01); *C01B 11/022* (2013.01); *A61L 2300/106* (2013.01); *A61L 2300/11* (2013.01); *A61L 2300/404* (2013.01)

(58) Field of Classification Search
CPC ......... A61K 33/40; A61K 47/02; A61L 15/46; A61L 2300/106; A61L 2300/11; A61L 2300/404; A61L 15/18; C01B 11/022; C01B 15/037
See application file for complete search history.

(56) References Cited

U.S. PATENT DOCUMENTS

| | | | | |
|---|---|---|---|---|
| 7,326,329 | B2 * | 2/2008 | Gomez | ..................... C25B 1/04 204/242 |
| 2008/0139674 | A1 * | 6/2008 | Archambeau | ........ A61K 9/0048 514/789 |
| 2010/0209360 | A1 * | 8/2010 | Suratt | ..................... A61K 33/00 424/49 |

OTHER PUBLICATIONS

Lin et al (International Journal of Hydrogen Energy, Jan. 2012, vol. 37, pp. 1311-1320).*

* cited by examiner

*Primary Examiner* — Mark V Stevens

(57) ABSTRACT

Peroxides and chlorine dioxide (compounds) can be stabilized for long periods of time (years) by combining the compounds with water that has been infused with dioxytetrahydride gas. Such stabilized materials can be used to infuse soft, solid substrates that can be used as sterile wipes, wound dressings, or the like.

8 Claims, No Drawings

METHOD OF STABILIZING COMPOUNDS IN WATER, WATER COMPOSITIONS THEREBY, AND ARTICLES CONTAINING SAID WATER COMPOSITIONS

This application is a continuation-in-part application claiming priority from U.S. Ser. No. 15/161,853, filed May 23, 2016, currently pending, which is a utility application claiming priority from U.S. Provisional application having Ser. No. 62/173,525, filed Jun. 10, 2015.

BACKGROUND OF THE INVENTION

Hydrogen peroxide ($H_2O_2$) in a water solution has long been recognized as a generally safe antimicrobial agent. However, hydrogen peroxide is thermodynamically unstable and decomposes to form water and oxygen. Consequently, the effectiveness of using hydrogen peroxide as a disinfectant has mixed results and causes hospitals and other medical institutions to resort to chlorine-based bleaches which have environmental and health safety concerns.

Hydrogen peroxide has historically been used in disinfecting topical wounds until researchers proved that it destroyed skin cells, slowed healing and led to scarring. Only very low concentrations of hydrogen peroxide in water solution should be applied topically to wounds but again the stability of the hydrogen peroxide is a concern as well as the residue left afterwards on the wound by surfactants and other chemicals used by chemists in trying to stabilize the very low concentrations of hydrogen peroxide in water.

Hydrogen peroxide is thermodynamically unstable and decomposes to form water and oxygen. Hydrogen peroxide is seen as an environmentally safe alternative to chlorine-based bleaches, as it degrades to form oxygen and water. It can be used for the disinfection of various surfaces and is generally recognized as safe as an antimicrobial agent by the U.S. Food and Drug Administration (FDA). However studies have found that when diluted with regular water, it only retains its efficacy for sterilization for a short amount of time. Hydrogen peroxide decomposes to a low level of residual activity within hours or a couple of days, and proves to be ineffective in certain cases and hospitals and other medical institutions are now being advised to use chlorine-based bleaches for disinfection.

Hydrogen peroxide demonstrates broad-spectrum efficacy against viruses, bacteria, yeasts, and bacterial spores and longer contact times are required for sporicidal activity.

Historically hydrogen peroxide has been used for disinfecting wounds, partly because of its low cost and prompt availability compared to other antiseptics. Only a very low concentration of $H_2O_2$ can induce healing, and only if not repeatedly applied. Surgical use can lead to gas embolism formation. Despite this it is still used for wound treatment in many developing countries. It is absorbed by skin upon contact and creates a local capillary embolism that appears as a temporary whitening of the skin.

Owing to the instability of hydrogen peroxide in water, it has become traditional for manufacturer's to put low concentrations of hydrogen peroxide (3%) in opaque bottles, or brown colored glass bottles, to preserve the stability. However, this only works for short periods of time.

THE INVENTION

What has now been discovered is that peroxides and chlorine dioxide (compounds) can be stabilized for long periods of time (years) by combining the compounds with water that has been infused with dioxytetrahydride.

Thus, this invention, in one embodiment, deals with a method of stabilizing a compound in water. The compounds are peroxides and chlorine dioxide. The method comprises combining a compound with water infused with dioxytetrahydride.

Dioxytetrahydride is a novel material produced by the methods set forth in U.S. patent application Ser. No. 15/627,688, filed Jun. 20, 2017, in the name of the inventor herein which is incorporated herein for what it teaches with regard to the manufacture of dioxytetrahydride and dioxytetrahydride gas infused water.

Another embodiment of this invention deals with a composition of matter comprising water infused with dioxytetrahydride gas and a compound selected from the group consisting of peroxides and chlorine dioxide.

Representative peroxides are, for example, hydrogen peroxide and benzoyl peroxide A further embodiment of this invention is an article, the article comprising a soft, solid substrate containing a composition as set forth Supra. Preferred soft, solid substrates are cotton and fabric gauze.

DETAILED DESCRIPTION OF THE INVENTION

Thus, this invention deals with water that has been infused with dioxytetrahydride gas and, hydrogen peroxide, in a concentration ranging between 0.1 weight % and 3 weight % that is used to moisten a soft, solid substrate prior to sealing it in an individual packet. Such soft, solid materials can be used, for example, as sterile wipes, for cleaning of topical wounds, and for removal of bandage adhesives from the skin, and the like.

In a first step of the method of preparing dioxytetrahydride gas, an aqueous fluid is provided to a reaction zone. While various aqueous fluids, such as distilled water, tap water, or water taken from a river, stream, lake or the like may be used to generate electrical current at satisfactory levels, it is preferred to use an electrochemical solution for the aqueous fluid of standardized composition so that the conditions of the method can be better standardized for maximum yield of gas.

The electrochemical solution is provided to a reaction zone which is preferably closed off so to allow the reaction to occur under pressure. The electrochemical solution is an electrolytic fluid comprising an alkali salt dissolved in distill water. Preferred alkali salts are tripotassium phosphate, potassium hydroxide, lithium hydroxide and sodium hydroxide. The specific gravity of the alkali salt in the solution is above 1.0 and not more than 1.3. Most preferably, potassium hydroxide is employed at a specific gravity from at least above 1.0 up to about 1.3. If another alkali salt is chosen other than potassium hydroxide a mole ratio must be calculated for that substance so that the maximum mole ratio represented by the specific gravity of 1.3 provided for potassium hydroxide will not be exceeded. These specific gravity values are as determined by a refractometer which provides readings that are temperature compensated. Most preferably, the electrochemical solution employed is tripotassium phosphate dissolved in distilled water at a concentration sufficient to form a solution having up to 1.3 specific gravity. A suitable refractometer is the Westover Model RHA-100, portable refractometer.

Electrochemical solution is contained in a receptacle which can be made out of a variety of materials including sheet steel, stainless steel, CV-PVC and epoxy-resin fiberglass. The apparatus and internal devices need to be heat resistant and waterproof. The reaction zone is comprised of said water as the electrochemical solution.

The electrochemical solution is placed in a reaction zone in the method of the invention. Overall, the method employs creation of a magnetic field in the electrochemical solution under conditions which do not provoke electrolysis of the electrochemical solution. Under these conditions, a single gas is generated and collected. This gas has desirable properties and is useful for applications.

In a first step of the method, a magnetic field is applied to the reaction zone. Preferably, the magnetic field is applied by providing a source of electric power to said reaction zone. An electric current in said reaction zone provides a magnetic field.

In a preferred embodiment, two metallic end plates, such as iron, having an inside surface and an outside surface, and having the capacity to conduct an electrical current are used in the reaction zone in opposing configuration. The inside of each end plate is partially submerged in the electrolyte solution. The metallic plates are preferably comprised of iron, but any metal can be used as long as such metal has the capacity to conduct an electric current and is preferably resistant to corrosion or erosion by alkali solutions. The distance between the plates should be ¼ inch or less. This distance is independent of the volume of the aqueous fluid employed or size of the reaction zone.

There is a relationship between the concentration of electrochemical solution and the amperage which will exist in the aqueous fluid upon application of current thereto. The higher the specific gravity, the greater the amperage will result. This will also affect the strength of the magnetic field, and increase the temperature of the solution. Electrolysis (used industrially to produce hydrogen gas via the reaction $2H_2O(l) \rightarrow 2H_2(g) + O_2(g)$) which is not desired in the method of this invention, could occur if the current is too high. In order for the magnetic field to be applied to the reaction zone, a power source (e.g., 110 volts DC) is applied respectively to the iron plates.

An appropriate power source that may be used in the method of the invention is 110 volt alternating current which has been converted to direct current using a rectifying process (e.g., a diode bridge device). Any standard power or voltage source may be used as long as it is rectified to direct current. When an electric current is applied to the reaction zone, a magnetic field is created in the reaction zone.

Overall, the method employs creation of a magnetic field in which two oxygens are forced into a diatomic bond with four hydrogens. Under these conditions two water molecules bind in a stable gaseous state and there is no electrolysis or breaking of either the hydrogen or oxygen bonds to each other. Under these conditions, a single gas is generated and collected.

The dioxytetrahydride gas generated by this method is then used to infuse water, the amount of infusion depending on the desired amount for a particular end use. Generally, the water is saturated with the gas.

This gas infused water is then treated with the desired peroxide or $ClO_2$ at the level desired, by merely mixing the peroxide with the water. The water is then used to moisten soft, solid substrates such as cotton or gauze and then the moistened substrates are individually packaged in packets for later use.

It is a unique property of the dioxytetrahydride gas infused water, that it stabilizes any peroxide or $ClO_2$ for long periods of time that enables one to treat soft, solid substrates that will last a long time.

EXAMPLES

Example 1

Peroxide test strips supplied by Indigo® Instruments, Part #33815-P100 (referred as "peroxide test strips" or "test strip" herein) were used to determine the amount of hydrogen peroxide in either distilled water or in water infused with dioxytetrahydride gas (referred as "dioxytetrahydride gas-infused water" or "ultra-pure polarized water" herein). Test Strips are capable of measuring peroxide concentrations between 1 and 100 ppm (parts per million). A peroxide test strip was first submerged into 3% water solution of hydrogen peroxide obtained from a drugstore for home use. The test strip showed a reading of 100 ppm for peroxide as expected.

A peroxide test strip was submerged into a clear PET-1 bottle (0.5 liter) of distilled water produced by Crystal Springs and another clear PET-1 bottle (0.5 liter) of dioxytetrahydride gas-infused water manufactured by AquaNew, LLC, Sarasota, Fla., respectively. The water produced by AquaNew is highly purified resulting from at least six (6) stages of treatment to obtain on or about 0.3 ppm of Total Dissolved Solids (pharmaceutical-grade water). No color change of each test strip was observed which indicates that peroxides were not present in either water sample even at the level of 1 ppm. Ten (10) drops of peroxide were added into each sample bottle and a test strip was dipped into each bottle and each bottle was immediately recapped. The contents of each bottle measured a concentration of 50 ppm of peroxide. Both bottles with closures were left on a shelf in open light conditions under climate controlled conditions with no direct sunlight.

After two weeks, a test strip was dipped into each bottle and the bottle was immediately recapped. The distilled water contents showed a decline from 50 to 30 ppm of peroxide. The dioxytetrahydride gas-infused water remained stable at 50 ppm. The two bottles with closures were placed back onto the shelf.

After four (4) months, another test strip was dipped into each bottle and the bottles were immediately recapped. The distilled water contents showed the lower 30 ppm measurement while the dioxytetrahydride gas-infused water held the peroxide concentration stable at 50 ppm.

While the mechanism of peroxide stability is not completely understood, dioxytetrahydride gas restructures highly purified water to maintain a neutral or lower pH and a relatively high Oxidation Reduction Potential (ORP) above +400. Initially at the introduction of the gas into the water, a negative ORP is measured which flips to the positive ORP within 24 hours of gassing the water. The theory is that the restructured water makes the hydrogen more accessible.

It appears the dioxytetrahydride gas-infused water has a low capacitance for intercellular communication, which alleviates pain and inflammation, and promotes healing on its own without the addition of any low concentration of hydrogen peroxide. The dioxytetrahydride gas-infused water has become a new effective and economical antibacterial and antifungal preparation in providing minimal infection potential, enhanced wound recovery and little to no side effects to wound trauma.

Example 2

Continuous experiments on the relative stabilization of hydrogen peroxide with different aqueous carriers, that is, types of water, including dioxytetrahydride gas-infused water, were carried out.

Very low concentrations of hydrogen peroxide (1.2 weight %) was added to the various aqueous carriers and measured for percent absorption by potassium permanganate titration.

The samples were tested on day 1, 20, 27 and 34. The tests were accelerated in aging when the temperature of each water sample was maintained at 58° C., approximating close to two years of stabilization.

The dioxytetrahydride gas-infused water samples prevent degradation of hydrogen peroxide at a temperature of 58° C. and maintain close to 100% absorption, that is, 1.2% concentration throughout the 34 days of testing. In comparison, hydrogen peroxide degraded in tap water at a temperature of 58° C. from 1.2% to 0.4% concentration on day 20 and below 0.2% concentration on day 34.

Example 3

Continuous experiments on the relative stabilization of chlorine dioxide with different aqueous carriers, that is, types of water, including dioxytetrahydride gas-infused water, were carried out.

A series of dilutions were set up and aged for 75 days at 50° C., (approximately two years of stability of this solution) that creates chlorine dioxide. A solution of chlorine dioxide at a concentration of 0.4 ppm was separately added to dioxytetrahydride gas-infused water and a second sample in tap water. The samples were aged for 75 days at 50° C. Prior to testing the concentration of chlorine dioxide of each sample, a control of chlorine dioxide at a concentration of 0.4 ppm in water was prepared. The concentration of chlorine dioxide measured in the two samples after aging, was 0.4 ppm for the dioxytetrahydride gas-infused water and 0.2 ppm for tap water.

The same protocol was performed on 0.2 ppm concentration of chlorine dioxide and the test results were 0.2 ppm for the dioxytetrahydride gas-infused water and 0.0 ppm in tap water.

The dioxytetrahydride gas-infused water was found to preserve chlorine dioxide at levels observed for chlorine dioxide in solution, freshly prepared.

What is claimed is:

1. A method of stabilizing a compound in water, said compound selected from the group consisting of:
    i. peroxides, and,
    ii. chlorine dioxide,
said method comprising:
    (I) preparing a gas by producing a reaction media comprising an aqueous electrochemical solution comprising one or more alkaline salts
    (II) placing the reaction media into a receptacle of an apparatus having a power supply that produces a magnetic field in a reaction zone via an electric current, wherein electrolysis does not occur in said reaction zone;
    (III) collecting the gas formed in said reaction zone after exposure to said magnetic field;
    (IV) infusing said collected gas into water to produce water infused with said collected gas;
    (V) combining said compound with the water infused with said collected gas to obtain a solution of the compound, wherein said compound in said solution is stabilized as compared to a solution of said compound in water that is not infused with said collected gas.

2. A composition comprising the stabilized compound in water produced in claim 1, wherein, when hydrogen peroxide is the peroxide, the amount of peroxide is at least 0.1 weight percent based on the total weight of the composition.

3. The composition of matter as claimed in claim 2 wherein the compound is used in the range of 0.1 weight percent to 3.0 weight percent based on the total weight of the water and the compound.

4. A composition as claimed in claim 2 wherein the peroxide is hydrogen peroxide.

5. A composition as claimed in claim 2 wherein the peroxide is benzoyl peroxide.

6. An article, said article comprising a soft, solid substrate containing a composition as claimed in claim 2.

7. An article as claimed in claim 6 wherein the soft, solid substrate is cotton.

8. An article as claimed in claim 6 wherein the soft, solid substrate is fabric gauze.

* * * * *